United States Patent [19]

Yamanishi et al.

[11] Patent Number: 4,613,465
[45] Date of Patent: Sep. 23, 1986

[54] TRIPHENYL METHANE DERIVATIVES AND METHOD OF QUANTITATIVELY MEASURING AN OXIDATIVE SUBSTANCE

[75] Inventors: Kazuhiko Yamanishi; Akinori Shintani; Satoru Okajima; Toshiro Hanada, all of Tokyo, Japan

[73] Assignee: Wako Pure Chemical Industries Ltd., Osaka, Japan

[21] Appl. No.: 649,477

[22] Filed: Sep. 11, 1984

[30] Foreign Application Priority Data

Mar. 2, 1984 [JP] Japan .................................. 59-40031

[51] Int. Cl.³ ............................................. C09B 11/10
[52] U.S. Cl. ..................................... 260/394; 436/135
[58] Field of Search ........................ 260/393, 394, 509

[56] References Cited

U.S. PATENT DOCUMENTS 1,470,554 10/1923 Craver ................................. 260/394
3,739,000 6/1973 Lodolini et al. .................... 260/394

Primary Examiner—Alan Siegel
Attorney, Agent, or Firm—Cushman, Darby & Cushman

[57] ABSTRACT

Disclosed herein is a novel compound which is excellent in solubility to water around a neutral range, stable in an aqueous solution state for a long period of time, and high in coloring sensitivity with a stable coloring development, and is represented by the general formula (I):

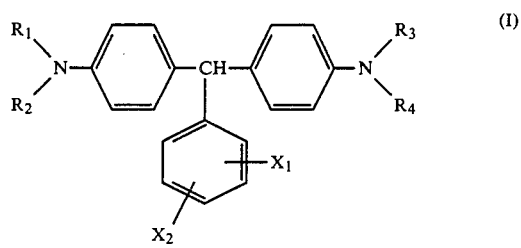

wherein $R_1$, $R_2$, $R_3$ and $R_4$, which may be the same as or different from one another, represent lower alkyl groups, and $X_1$ and $X_2$ both represent $-O(CH_2)_nSO_3M$ in which M is a hydrogen atom, an alkali metal ion or $NH_4^+$, and n is an integer of 2–4, or either of $X_1$ and $X_2$ represents $-O(CH_2)_nSO_3M$ in whch M and n are the same meanings as given above and the other represents a hydrogen atom. This reagent is hardly susceptible of the influence of the serum components such as hemoglobin, bilirubin and so on due to its color having absorption on a longer wavelength side. Disclosed is also a method of quantitatively measuring an oxidative substance, particularly, hydrogen peroxide, by using this color test reagent.

4 Claims, 4 Drawing Figures

TRIPHENYL METHANE DERIVATIVES AND METHOD OF QUANTITATIVELY MEASURING AN OXIDATIVE SUBSTANCE

BACKGROUND OF THE INVENTION

1. Field of the Invention

The present invention relates to a novel triphenyl methane derivative and a method of quantitatively measuring an oxidative substance by using said derivative as a coloring component.

2. Description of the Prior Art

Since changes in components of body fluids such as blood, urine and the like are deeply correlated with diseases, measurement of the body fluid components has been important to diagnose the diseases, solve pathological conditions and judge a therapeutic course. For instance, as well known, there have been developed methods of measuring an extremely various kinds of micro-components including cholesterol, triglyceride, glucose, uric acid, monoamine oxidase, bile acid and the like in the blood, and they have been used for the diagnosis of the diseases.

At present, as a method of measuring serum components there is generally popularized a so-called "enzyme method" in which an enzyme reaction is carried out by using an enzyme specifically acting upon an intended component, and a product formed thereby is measured to determine the content of the intended component. With development of oxidizable coloring reagents, there have been increasingly developed and used, for example, a method in which an oxidizable coloring reagent is oxidized with a peroxidase-like substance and an oxidative substance to be led to a coloring system, among them, a method in which an $H_2O_2$ generating enzyme, for instance, an oxidase, is applied to generate $H_2O_2$ in such an amount as to meet with that, of an intended component, and the generated $H_2O_2$ is led to a coloring system with use of a peroxidase and an oxidizable coloring reagent as a coloring component to determine the amount of the intended component through colorimetric determination. That is, there may be recited by way of example a method in which $H_2O_2$ generated with a combined use of cholesterol-cholesterol oxidase, glucose-glucose oxidase, triglyceride-lipoprotein lipase-glycerol oxidase, uric acid-uricase, or the like is led to a coloring system by using peroxidase and an oxidizable coloring reagent and a color development is measured by using an photometer to determine the amount of an intended component. As a matter of course, the concentrations of the components in the serum differ depending upon kinds of the components, and therefore the amounts of $H_2O_2$ generated through the enzyme reaction varies over a wide range. Accordingly, there have been developed and used oxidizable coloring reagents with sensitivities meeting the intended purposes. For example, an oxidizable coloring reagent combining 4-aminoantipyrine with phenolic compound or N,N-dialkylaniline compound are generally used in the measurement of cholesterol, triglyceride, glucose, uric acid or the like.

Meanwhile, among the body fluid components, there are some components which are contained in the normal serum in an extremely small amount, like monoamine oxidase and bile acid. That is, the monoamine oxidase is an enzyme which acts upon a monoamine compound to generate $H_2O_2$ and aldehyde, but the amount of the generated $H_2O_2$ is extremely small due to its extremely small concentration in the serum. Thus, the oxidizable coloring reagents of the above combinations are insufficient in sensitivity to quantitatively determine such components. Consequently, an oxidizable coloring reagent with a higher sensitivity is being demanded. Under these circumstances, there has heretofore been developed and used in a commercial base a measuring method using a derivative of leucomethylene blue as the oxidizable coloring reagent with a higher sensitivity. However, this leuco coloring matter has the defect that it is questionable in stability in a solution state, and that a coloring reagent containing this leuco coloring matter is gradually colored during storage.

Further, although for the similar purpose to the above, there have been studied a leucocrystal violet, a leuco malachite green and so on as an oxidizable coloring reagent with high sensitivity which belong to the same triphenyl methane type leuco coloring matters as in the present invention, all of them are difficult to dissolve into water in around the neutral range. Therefore, it is difficult to dissolve them in a desired concentration. Thus, they are insuitable for the measurement of a micro-component.

As a leuco coloring matter improved in this defect, there is proposed bis(4-diethylaminophenyl)-2-sulfophenyl methane (hereinafter abbreviated as BSPM) (Japanese patent application Laid-Open No. 26199/1981). However, it can not necessarily be said that the solubility thereof to water is sufficient.

SUMMARY OF THE INVENTION

It is an object of the present invention to provide a novel compound which is excellent in solubility to water in around the neutral range and stable in an aqueous solution for a long period of time, and has a high coloring sensitivity and a stable coloring.

It is another object of the invention to provide a novel compound which indicates coloring which has an absorption in a longer wavelength side and therefore is hardly susceptible to influences by serum components such as hemoglobin, bilirubin and the like.

Still another object of the invention is to provide a method of quantitatively measuring an oxidative substance, particularly $H_2O_2$, by using such a novel coloring reagent.

According to the present invention, there is a provision of a novel compound of a triphenyl methane derivative represented by the general formula (I):

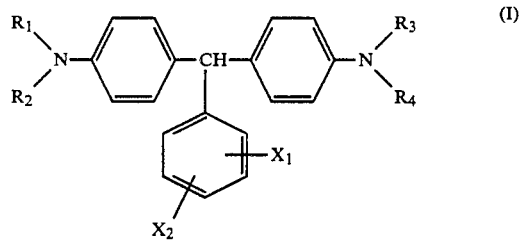

wherein $R_1$, $R_2$, $R_3$ and $R_4$, which may be the same as or different from one another, represent lower alkyl groups, and $X_1$ and $X_2$ both represent $-O(CH_2)_nSO_3M$ in which M is a hydrogen atom, an alkali metal ion or $NH_4^+$, and n is an integer of 2-4, or either of $X_1$ and $X_2$ represents $-O(CH_2)_nSO_3M$ in which M and n are the same meanings as given above and the other represents a hydrogen atom.

According to another aspect of the invention, there is a provision of a method of quantitatively measuring an oxidative substance by using as a coloring component a triphenyl methane derivatives of the general formula (I) as given above.

These and other objects, features, advantages of the invention will be well appreciated when taken in conjunction with the attached drawings with understanding that some modifications, variations, and changes would be easily done by the skilled in the art to which the invention pertains without departing from the spirit of the invention or the scope of the appended claims.

DETAILED DESCRIPTION OF THE INVENTION

Figure 1:
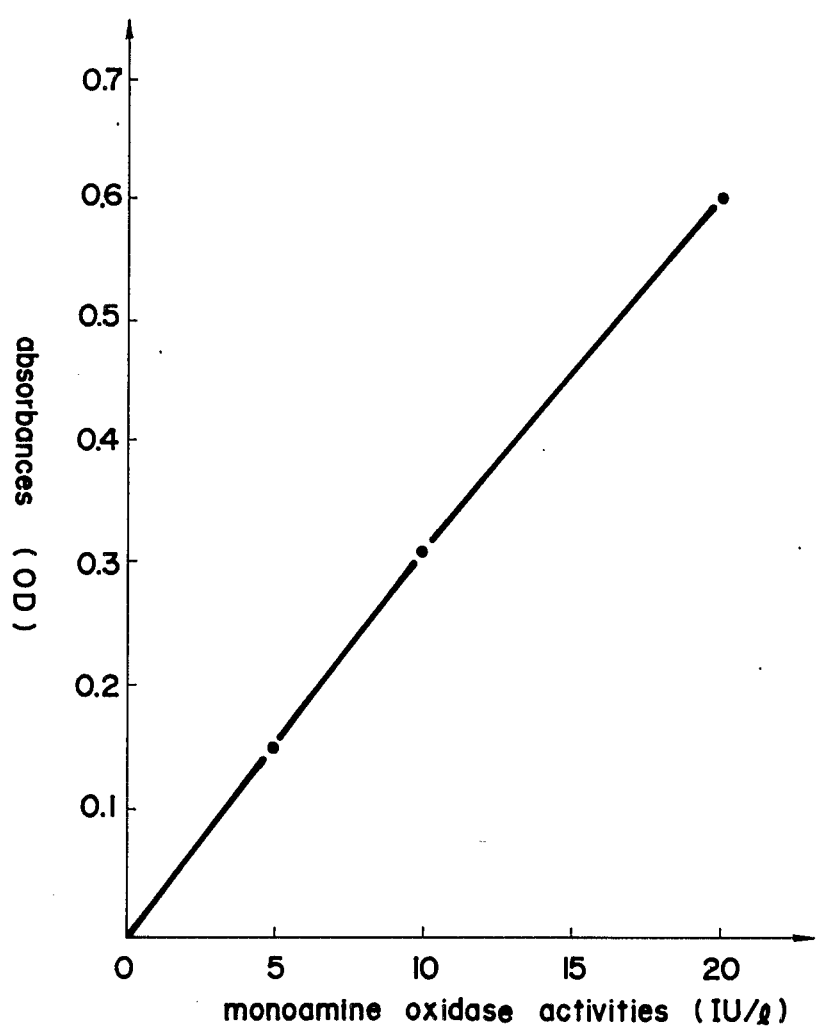
FIG. 1 shows a calibration curve obtained in Example 3 in which absorbances (OD) are plotted in an ordinate with respect to the respective monoamine oxidase activities (IU/l) in an abscissa, and plotted points are connected.

The present invention relates to a novel triphenyl methane derivative represented by the following general formula (I):

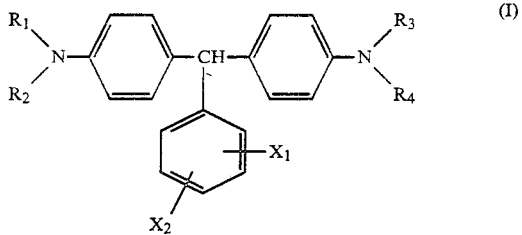

wherein $R_1$, $R_2$, $R_3$ and $R_4$, which may be the same as or different from one another, represent lower alkyl groups, and $X_1$ and $X_2$ both represent $-O(CH_2)_nSO_3M$ in which M is a hydrogen atom, an alkali metal ion or $NH_4^+$, and n is an integer of 2–4, or either of $X_1$ and $X_2$ represents $-O(CH_2)_nSO_3M$ in which M and n are the same meanings as given above and the other represents a hydrogen atom.

The invention also relates to a method of quantitatively measuring the amount of an oxidative substance, particularly hydrogen peroxide by using said triphenyl methane derivatives as a coloring component.

In the triphenyl methane derivatives represented by the general formula (I) according to the present invention, $R_1$–$R_4$ represent a lower alkyl groups such as methyl, ethyl, propyl, etc., and they may be the same as or different from one another. M in $-O(CH_2)_nSO_3M$ denoted by $X_1$ and $X_2$ is a hydrogen atom, an alkali metal ion such as $Na^+$, $K^+$, $Li^+$, etc., or $NH_4^+$, and n is 2, 3 or 4.

It is considered that the triphenyl methane derivatives represented by the general formula (I) according to the present invention are novel compounds which have not been described in the literatures, and the triphenyl methane derivatives may generally be produced by the following process.

That is, for instance, in the case of bis(4-N,N-diethylaminophenyl)-3,4-disodium sulfopropoxyphenyl methane, protocatechualdehyde and propane sultone are reacted with each other under heating in an organic solvent such as methyl cellosolve, ethyl cellosolve or the like in the presence of an alkali such as caustic soda, sodium alcoholate or the like, and after the completion of the reaction, ordinary post-treatments such as cooling, crystal precipitation, solvent pouring, filtration, washing and so on are carried out, and if necessary, purification by a column chromatography or the like is carried out to obtain 3,4-disodium sulfopropoxybenzaldehyde. Then, the resultant is reacted with N,N-diethylaniline in an organic solvent such as methyl cellosolve, ethyl cellosolve or the like under heating in the presence of a catalyst such as zinc chloride or the like, and post-treatments are done in the ordinary way and purification is carried out by a column chromatography or the like to obtain the intended product. Generally, the other compounds encompassed by the general formula (I) may be produced in the same or similar manner.

The triphenyl methane type leuco coloring matters represented by the general formula (I) according to the present invention have first been synthesized by the present inventors to improve the inferior solubility to water around a neutral range, which is the defect of the known triphenyl methane type leuco coloring matters such as leucomalachite green, leucocrystal violet and so on, and is chiefly characterized in that a group of $-O(CH_2)_nSO_3M$ (M and n represent the same meanings as given above) is introduced as a solubilizing group.

Namely, the above BSPM is a triphenyl methane derivative in which one sulfonic acid group is introduced into a benzene nucleus to improve solubility of the triphenyl methane type leuco coloring matter, but its solubility at pH 7.2 is 0.5 mM. Thus, it cannot be said that the solubility to water around the neutral range is sufficient. In the case with bis(4-diethylaminophenyl)-2,4-disulfophenyl methane in which two sulfonic acid groups are introduced into a benzene nucleus, although the solubility to water is obviously improved, it cannot be oxidized in a $H_2O_2$-POD (peroxidase) system due to its high oxidation-reduction potential, so that no coloring takes place. Therefore, this compound cannot be used in a body fluid component-measuring method in which $H_2O_2$ is generated by using an enzyme, and is led to a coloring system for the measurement of an intended component.

To the contrary, according to the triphenyl methane derivative of the present invention, even ones attached with a single $-O(CH_2)_nSO_3M$ (M and n are the same as given above), for example, bis(4-N,N-diethylaminophenyl)-4-sodium sulfopropoxyphenyl methane (hereinafter abbreviated as BSproPM) exhibits 5 mM in the solubility to water around the neutral range (pH 7.2) which is 10 times as large as that of BSPM, and the derivatives having two —O(CH$_2$)$_n$SO$_3$M groups, for example, bis(4-N,N-diethylaminophenyl)-3,4-disodium sulfopropoxyphenyl methane (hereinafter abbreviated as BSdiproPM) is more soluble and exhibits a solubility of not less than 30 times (15 mM or more) that of BSPM. Though quite unexpected, the triphenyl methane derivatives according to the present invention in which two groups represented by —O(CH$_2$)$_n$SO$_3$M (M and n are the same meanings as given above), different from the triphenyl methane derivative in which two sulfonic acid groups are directly bonded to the benzene nucleus, is extremely excellent in oxidation coloring in the H$_2$O$_2$-POD system, and can be satisfactorily used for the purpose aimed at by the present invention.

The leuco coloring matter according to the present invention is extremely stable in a solution state. While an aqueous solution of the conventional leucomethylene blue derivative becomes unusable at room temperature in several hours, the aqueous solution of the leuco coloring matter according to the present invention does not change at all even in a 24 hour storage, and therefore is exceedingly useful as coloring component.

Every leuco coloring reagent according to the invention has an coloring sensitivity of as high as 80,000, and uniformly has the $\lambda_{max}$ value on a long wave length side, that is, at 600–700 nm, so that they are hardly susceptible of interference with hemoglobin, bilirubin and the like.

Further, coloring caused by the coloring matters according to the invention is extremely stable, and almost no color fading is observed.

As mentioned above, since the triphenyl methane derivatives according to the invention has various merits, the derivatives can be so effectively used in the known measuring method in which the triphenyl methane derivatives is oxidized with an oxidative substance such as H$_2$O$_2$ and peroxidase or a peroxidase-like substance such as hemoglobin to be led to a coloring system so as to quantitatively determine the amount of the intended component, for example, in the case of the measurement of the body fluid components such as blood, urine and the like according to the enzyme method (H$_2$O$_2$ generating system), and in the measurement of hemoglobin in the serum by using H$_2$O$_2$ or an oxidative substance such as sodium perborate.

In general, although the oxidizable coloring reagent of the triphenyl methane type (triphenyl methane type leuco coloring matter) undergoes coloring-inhibition with uric acid and protein, Yamanishi and Hanada of the present inventors have found that in the practice of the present invention, the influence of uric acid can be avoided under co-existence of uricase (in this case, uric acid is decomposed without being accompanied by the generation of H$_2$O$_2$), while the influence of protein can be avoided through addition of a metal chelate or a specific surface active agent.

That is, the leuco coloring matter according to the present invention can be used for the measurement of chemical components in body fluids such as the serum or the blood containing the acid or protein according to the enzyme method (H$_2$O$_2$ generating system) without any trouble.

In the measurement according to the enzyme method (H$_2$O$_2$ generating system) using the triphenyl methane type leuco coloring matter of the invention as the coloring component, as the chemical components in the body fluids which can be measured, mention may be made of all items which are measured according to the conventional enzyme method (H$_2$O$_2$ generating system), for instance, glucose, free cholesterol, whole cholesterol, HDL (high specific density lipoprotein)-cholesterol, LDL (low specific density lipoprotein)-cholesterol, triglyceride, phospholipid, uric acid, monoamine oxidase and so on (In the case of uric acid, it is necessary that uricase is preliminarily acted upon uric acid to generate H$_2$O$_2$, and then the coloring reagent according to the present invention is added together with peroxidase for color development). Among them, the coloring reagent according to the present invention is particularly suited for the measurement of a component contained in the body fluids in an extremely small amount, for example, monoamine oxidase, and bile acid.

As the surface active agent used for removing the influence of the protein, use may be made of, for instance, Emal NC (polyoxyethylene alkylphenyl ether sulfate), manufactured by Kao Atlas Co., Ltd.; trademark), Sunnol 605 D (polyoxyethylene alkyl ether sulfate, Lion Yushi Co., Ltd.; trademark). As the metal chelate, use may be made of Fe(III)-EDTA, NI(II)-EDTA and the like.

When the method according to the present invention is applied to the serum, the triphenyl methane type oxidizable coloring agent may be used in a concentration of 0.01 mM or more, and ordinarily, the concentration of 0.02–0.3 mM is preferably adopted.

The concentration of uricase used to avoid the influence of the uric acid may be generally not lower than 50 U/l, and ordinarily a range of 100–500 U/l is preferably adopted. It is preferable to adopt the concentrations of the surface active agent and the metal chelate for avoid the influence of the protein in ranges of 0.05–1.0% and 0.01–0.5% respectively.

The pH of the coloring reagent liquid may be ordinarily 5–9, and pH=6–9 which is suitable for the enzyme reaction is more preferable from the standpoint of color development and stability.

The invention will be explained more in detail with reference to the following examples:

EXAMPLE 1

SYNTHESIS OF BSdiproPM (i) Synthesis of 3,4-disodium sulfopropoxybenzaldehyde To 27.6 g (0.2 mol) of protocatechualdehyde dissolved into 200 ml of methanol was added 92.4 g (0.48 mol) of 28% sodium methylate, which was concentrated to dryness. 400 ml of methyl cellosolve was added to the thus dried matter, which was dissolved under stirring. Then, 58.8 g (0.48 mol) of propanesultone dissolved into 50 ml of methyl cellosolve was dropwise added to the solution at 95°–100° C., and after the completion of the addition, the reaction was carried out at the same temperature under stirring for one hour. After cooling of the reaction liquid, acetone was added thereto to disperse crystals, and the crystals were filtered out, followed by drying, to obtain 88 g of crude crystals (yield 103.2%). The crude product was purified by a column chromatography (ODS reversed phase column chromatography, 20 % methanol aqueous solution containing 5 % of AcOH) to obtain 43.5 g of purified crystals (yield 51.0%). TLC: one spot, IR (KBr): $\nu = 1055$(—SO$_3^\ominus$, $\phi$—O—R), 1190–1220 (—SO$_3^\ominus$, $\phi$—O—R), 1670 cm$^{-1}$(—CHO).

(ii) Synthesis of BSdiproPM

After 7.0 g (16.4 mmol) of the 3,4-disodium sulfopropoxybenzaldehyde obtained in (i), 7.3 g (49.2 mmol) of N,N-diethylaniline and 4.5 g of zinc chloride were suspended into 140 ml of methyl cellosolve, reaction was carried out at an internal temperature of 125° C. for 28 hours. During the reaction, produced water was distilled off. After the termination of the reaction, 300 ml of dimethyl sulfoxide was added to dissolve the reaction product, and insoluble matters were filtered off. 1,700 ml of ethyl acetate was added to the filtrate to precipitate crystals. The crystals were filtered out, and were dissolved into 15 ml of water. This solution was subjected to purification by a column chromatography (carrier Wakogel® C-200), and the eluent was subjected to the distillation. The residue was dissolved in water, which was decolorized and filtered. After concentration of the filtrate, acetone was added to the concentrate to precipitate crystals, which was filtered out to obtain 2.68 g of the intended fine slightly blue crystals (yield: 23.2 %).

| (Elementary Analysis) | | | |
|---|---|---|---|
| | H | C | N |
| Calculated (%) | 6.27 | 56.08 | 3.96 |
| Found (%) | 6.46 | 56.06 | 4.14 |

UV (0.1 M tris buffer solution, pH=7.5): $\lambda_{max}(\epsilon)=620$ nm (166,300). IR (KBr): $\nu=1020-1030$ ($—SO_3^{\ominus}$, $\phi—O—R$), 1180-1200 ($—SO_3^{\ominus}$, $\phi—O—R$), 1380 [$—N—(C_2H_5)_2$], 2950 cm$^{-1}$ ($—C_2H_5$).

EXAMPLE 2

SYNTHESIS OF BSproPM

In accordance with Example 1 (ii), 2.5 g of 4-sodium sulfopropoxybenzaldehyde obtained from p-hydroxybenzaldehyde and propanesultone similarly to Example 1 (i) was reacted with 3.4 g of N,N-diethylaniline in 50 ml of methyl cellosolve in the presence of 2.4 g of zinc chloride, and post-treatment was carried out similarly to Example 1 (ii) to obtain 0.7 g of light blue crystals of 0.7 g of bis(4-N,N-diethylaminophenyl)-4-sodium sulfopropoxyphenyl methane (BSproPM) (yield: 13.6 %).

| (Elementary Analysis) | | | |
|---|---|---|---|
| | H | C | N |
| Calculated (%) | 7.19 | 65.91 | 5.12 |
| Found (%) | 7.33 | 65.94 | 5.28 |

UV (0.1 M tris buffer solution, pH=7.5): $\lambda_{max}(\epsilon)=620$ nm (121,800).

EXAMPLE 3

Measurement of serum monoamine oxidase activity

Using 15 mM of allylamine as a substrate, uricase, BSdiproPM, Emal NC (Kao Atlas Co., Ltd.; trademark) and POD were dissolved into 20 mM of phosphate buffer solution (pH =7.0) to be in the respective concentrations of 200 U/l, 0.03 mM, 5% and 3,000 U/l to prepare a substrate color test liquid.

8.9 mM aqueous solution of sodium diethyldithiocarbamate was prepared as a reaction termination liquid.

3 ml of the above substrate color test liquid was added to 50 μl of a sampled serum, and incubated at 37° C. for 30 minutes. Then, 50 μl of the reaction terminator liquid was mixed thereinto and absorbance at a wavelength of 620 nm was measured by using a reagent blank as control.

Using bovine monoamine oxidase manufactured by Sigma Co., Ltd., standard liquids of 5 IU/l, 10 IU/l and 20 IU/l were prepared, and then absorbances were measured with respect to these standard liquids as in the case of the serum to obtain a calibration curve therefrom, which is shown in FIG. 1.

The activity of monoamine oxidase in the sample was determined from the calibration curve.

REFERENCE EXAMPLE 1

(Buffer solution)

30 mM of allylamine, 0.53 mM of phenol, and an appropriate amount of a surface active agent were added to 25 mM of Good buffer solution (pH 6.75) to prepare a buffer solution.

(First test liquid)

170 units of lipoprotein lipase, 425 units of ascorbate oxidase, 255 units of peroxidase and an appropriate of a stabilizer were added to 85 ml of the above prepared buffer solution to prepare a first test liquid.

(Second test liquid)

7.3 μmol of 10-N-methylcarbamoyl-3,7-dimethylamino-10H-phenothiazine (MCDP) and an appropriate amount of a stabilizer were added to 85 ml of the above prepared buffer solution to prepare a second test liquid.

When in use, the first test liquid and the second test liquid were mixed with each other in the same volume to prepare a color test liquid.

An aqueous solution of 8.9 mM of sodium diethyldithiocarbamate was prepared as a reaction termination liquid.

3.0 ml of the color test liquid was taken, and preliminarily incubated in the constant temperature chamber at 37° C. for about 5 min., and 50 μl of serum was added thereto, incubated at 37° C. for 30 min. Then, 50 μl of the reaction terminator liquid was added to and mixed with the reaction solution, and absorbance (Es) at a wavelength of 660 nm was measured with reference to water as control.

By using 50 μl of monoamine oxidase standard liquids (prepared in Example 3) and 50 μl of purified water instead of the serum, absorbances Estd and $E_B$ were obtained as in the same procedure as above, and the activity of the monoamine oxidase was calculated by the following formula:

Monoamine oxidase activity (IU/l) =

$$\frac{E_s - E_B}{E_{std} - E_B} \times \text{standard enzyme activity}$$

Table 1 shows changes in the reagent blank in the storage of the color test liquid (stored at 15° C.) in the cases of Example 3 and Reference Example 1.

TABLE 1

| Stored time (hour) | Example 3 | Reference Example 1 |
|---|---|---|
| 0 | 0.030 | 0.027 |
| 2 | 0.030 | 0.041 |
| 5 | 0.029 | 0.124 |
| 7 | 0.030 | 0.172 |

TABLE 1-continued

| Stored time (hour) | Example 3 | Reference Example 1 |
|---|---|---|
| 24 | 0.031 | could not be measured |

As shown in Table 1, in the case of Reference Example 1, since the reagent is increasingly colored during the storage of the color test liquid and the reagent blank increases with lapse of time, it is necessary to prepare a fresh color test liquid when in use. To the contrary, the color test liquid according to the present invention underwent no color change even after 24 hours.

Table 2 shows comparison in measurement results between Example 3 and Reference Example 1.

TABLE 2

| Serum No. | Example 3 (IU/l) | Reference Example (IU/l) |
|---|---|---|
| 1 | 1.5 | 1.7 |
| 2 | 7.8 | 7.2 |
| 3 | 2.3 | 2.3 |
| 4 | 1.1 | 1.4 |
| 5 | 4.2 | 3.9 |
| 6 | 1.6 | 1.6 |
| 7 | 5.1 | 4.8 |
| 8 | 12.7 | 13.0 |
| 9 | 0.9 | 1.1 |
| 10 | 1.2 | 1.0 |
| average | 3.84 | 3.80 |

As shown in Table 2, the values in Example 3 are well correlated with Reference Example 1, and no significant differences therebetween are observed ($\gamma=0.997$).

EXAMPLE 4

Quantitave analysis of free cholesterol in serum

To 0.05 M of phosphate buffer solution (pH 7.0) were dissolved BSdiproPM, uricase, cholesterol oxidase, peroxidase, Triton X-100, and Emal NC, to be at concentrations of 0.05 mM, 300 U/l, 100 U/l, 3000 U/l, 0.15% and 0.05% respectively to prepare a color test liquid.

3 ml of the above color test liquid was added to 10 μl of sampled serum, which was incubated at 37° C. for 10 min. Then, absorbance at a wavelength of 620 nm was measured with reference to a reagent blank as control.

Figure 2:
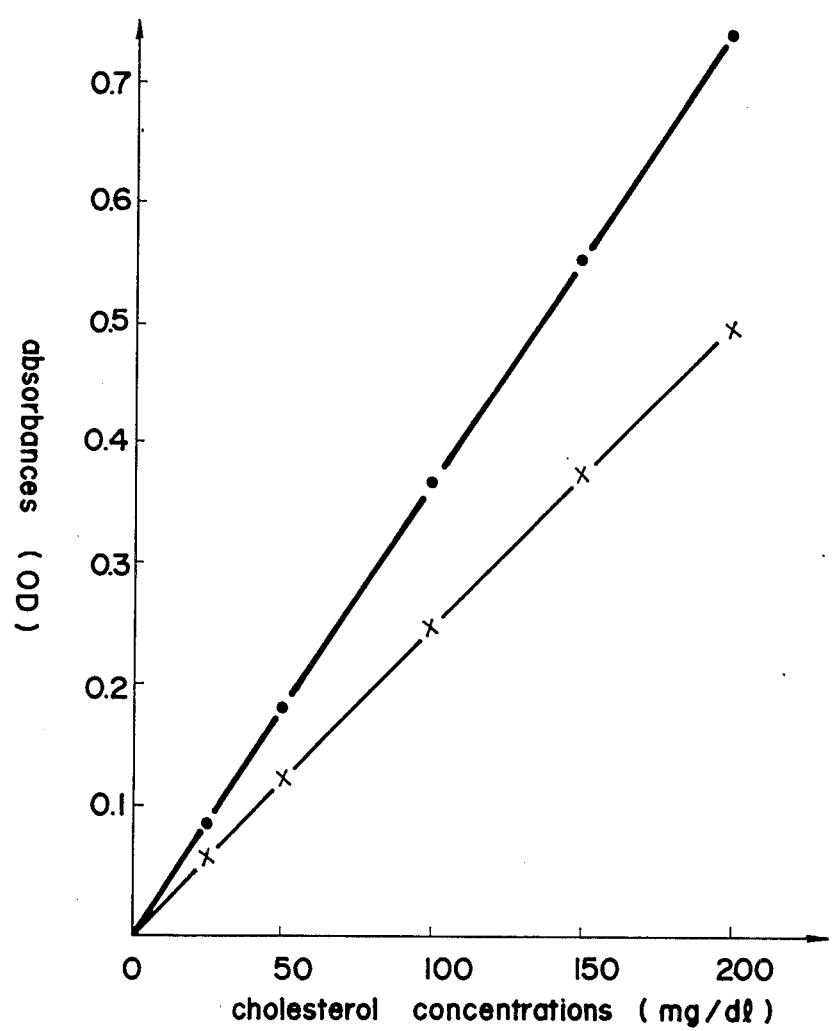
FIG. 2 shows calibration curves obtained in Example 4 and Reference Example 2 respectively ( - being the calibration curve in Example 4 and x—x being the one in Reference Example 2) in which absorbances (OD) are plotted in an ordinate with respect to the respective cholesterol concentrations (mg/dl) in an abscissa, and the plotted points are connected.

Separately, cholesterol standard liquids were prepared to be at concentrations of 25, 50, 100, 150 and 200 mg/dl respectively, and absorbances were measured in the same manner as in the serum to obtain a calibration curve therefrom. FIG. 2 is shows a calibration curve.

The concentration of the cholesterol in the serum was determined from the calibration curve.

REFERENCE EXAMPLE 2

Quantitative Analysis of free cholesterol in serum

To 0.05 M phosphate buffer liquid (pH =7.0) were dissolved 4-aminoantipyrine, phenol, cholesterol oxidase, peroxidase, and Triton X-100 to be concentrations of 0.01%, 0.1%, 100 U/l, 3,000 U/l and 0.1% respectively to prepare a color test liquid.

3 ml of the above color liquid was added to 50 μl of sampled serum, which was incubated at 37° C. for 10 min. Then, absorbance at a wavelength of 505 nm was measured with reference to a reagent blank as control.

Separately, color was developed by using the cholesterol standard solutions (prepared in Example 4) in the same manner as above, and absorbances were measured to obtain a calibration curve therefrom. FIG. 2 shows the thus obtained calibration curve.

Table 3 shows comparison in measurement results between Example 4 and Reference Example 2.

TABLE 3

| Serum No. | Measured value of cholesterol | | | Uric[2] acid concentration |
|---|---|---|---|---|
| | Example 4 mg/dl | Reference Example 2 mg/dl | No[1] uricase | |
| 1 | 41.8 | 43.1 | 20.7 | 4.1 |
| 2 | 34.0 | 34.7 | 5.4 | 8.5 |
| 3 | 40.8 | 43.1 | 17.0 | 4.8 |
| 4 | 29.3 | 30.6 | 6.2 | 5.7 |
| 5 | 62.3 | 62.1 | 35.2 | 6.3 |
| 6 | 64.6 | 63.3 | 40.6 | 4.3 |
| 7 | 27.8 | 28.6 | 1.7 | 9.3 |
| 8 | 54.1 | 50.4 | 22.9 | 5.2 |
| Average | 44.34 | 44.49 | | |

Note:
[1]"No uricase" means a case where measurement was carried out according to Example 4 with respect to a color test liquid prepared from the components of the color test liquid of Example 4 with uricase being excluded therefrom.
[2]"Uric acid concentration" means the concentration of the uric acid meausured by using Uric Acid B-Test wako (Manufactured by Wako Pure Chemical Industries, Ltd.)

The significant difference in the measurement values between Example 4 and Reference Example 2 was examined using t-test. The significance level was 5%, and no difference therebetween was observed. In the case of "no uricase", the measurement values were largely lowered due to the uric acid in the serum, and negative influence due to the uric acid is obvious.

EXAMPLE 5

Quantitative analysis of hydrogen peroxide

To 0.05 M phosphate buffer solution (pH=7.0) were dissolved BSdiproPM, peroxidase and Triton X-100 to be at concentrations of 0.05 mM, 3,000 U/l and 0.5% respectively to prepare a color test liquid.

3 ml of the above color test liquid was added to 20 μl of a sample containing 1–60 ppm of $H_2O_2$, which was incubated at 37° C. for 10 min. Then, absorbance at a wavelength of 620 nm was measured with reference to a reagent blank as control.

Figure 3:
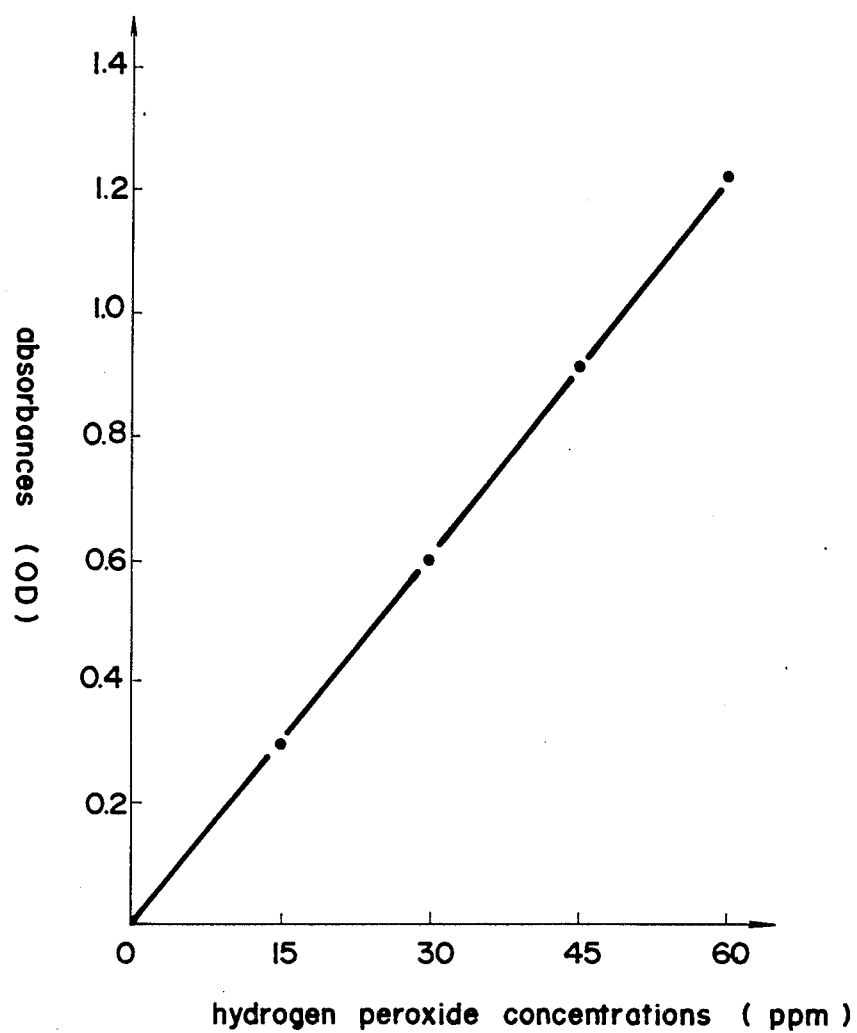
FIG. 3 shows a calibration curve obtained in Example 5 in which absorbances (OD) are plotted in an ordinate with respects to the respective hydrogen peroxide concentrations (ppm) in an abscissa, and the plotted points are connected.

Separately, by using hydrogen peroxide standard solutions prepared to be at concentrations of 15, 30, 45, and 60 ppm respectively were prepared, absorbances thereof were measured in the same manner as above to obtain a calibration curve therefrom. FIG. 3 shows the thus obtained calibration curve.

The concentration of the hydrogen peroxide in the sample was determined from the calibration curve of hydrogen peroxide.

EXAMPLE 6

Quantitative Analysis

To 0.05 M of phosphate buffer solution (pH=7.0) were dissolved BSproPM, peroxidase, and Triton X-100 to be at concentration of 0.05 mM, 3,000 U/l and 0.05% respectively to prepare a color test liquid.

Absorbance of the sample was measured in the same manner as in Example 5, and the concentration of the hydrogen peroxide in the sample was determined from a calibration curve obtained by using the separately prepared hydrogen peroxide standard solution (used in Example 5).

Figure 4:
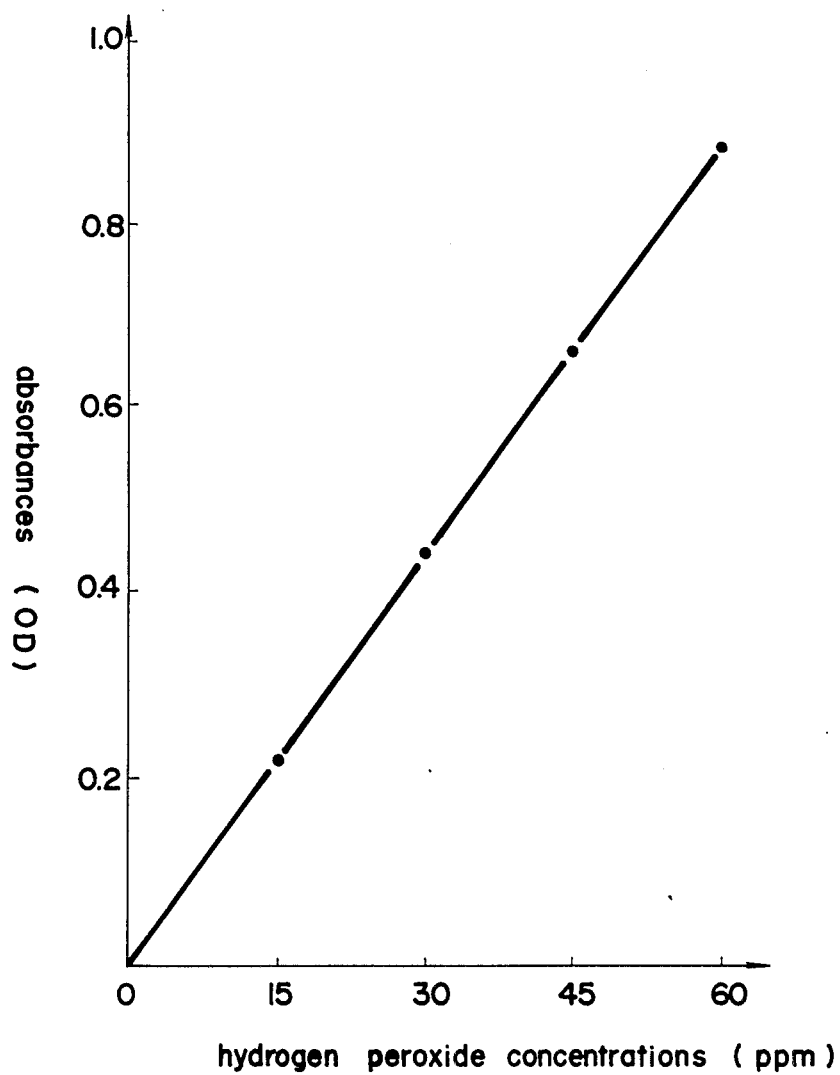
FIG. 4 shows a calibration curve obtained in Example 6 in which absorbances (OD) are plotted in an ordinate with respect to the respective hydrogen peroxide concentrations (ppm) in an abscissa, and the plotted points are connected.

FIG. 4 shows the calibration curve thus obtained.
What is claimed is:

1. A triphenyl methane derivative represented by the general formula (I):

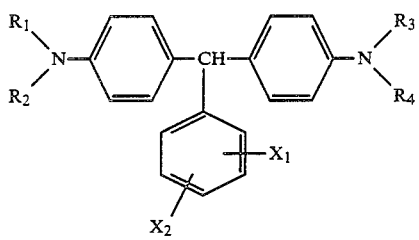

wherein $R_1$, $R_2$, $R_3$ and $R_4$, which may be the same as or different from one another, represent lower alkyl groups, and $X_1$ and $X_2$ both represent $-O(CH_2)_nSO_3M$ in which M is a hydrogen atom, an alkali metal ion or $NH_4^+$, and n is an integer of 2–4, or either of $X_1$ and $X_2$ represents $-O(CH_2)_nSO_3M$ in which M and n are the same meanings as given above and the other represents a hydrogen atom.

2. The triphenyl methane derivative according to claim 1, wherein both of $X_1$ and $X_2$ represent $-O(CH_2)_nSO_3M$.

3. The triphenyl methane derivative according to claim 1, wherein either of $X_1$ and $X_2$ represents $-O(CH_2)_nSO_3M$, and the other represent a hydrogen atom.

4. The triphenyl methane derivative according to claim 1, wherein the derivative is bis(4-N,N-diethylaminophenyl)-4-sodiumsulfopropoxyphenyl methane or bis(4-N,N-diethylaminophenyl)-3,4-disodium sulfopropoxyphenyl methane.

* * * * *